United States Patent [19]

Anderson

[11] Plant 4,790

[45] Nov. 17, 1981

[54] NECTARINE TREE

[76] Inventor: Frederic W. Anderson, 826 W. 22nd St., Merced, Calif. 95340

[21] Appl. No.: 187,849

[22] Filed: Sep. 15, 1980

[51] Int. Cl.[3] ..... A01H 5/03

[52] U.S. Cl. ..... Plt./41

[58] Field of Search ..... Plt./41

*Primary Examiner*—Robert E. Bagwill

*Attorney, Agent, or Firm*—Roger B. Webster

[57] ABSTRACT

A nectarine tree which is of large-medium size, spreading, hardy, foliated with large, lanceolate, acutely pointed leaves having a crenate margin, medium length petiole, and medium size, alternate, reniform glands, blooms early-medium from hardy, medium length, pointed flower buds, the flowers being large and pink, and the tree is a regular and productive bearer of large, early-ripening, uniform, symmetrical, globose-oblong fruit which is freestone when fully ripe, the fruit having a yellow ground color substantially overspread and highly colored with a dark red, and the flesh is yellow.

1 Drawing Figure

CLASSIFICATION OF THE VARIETY

The present variety of nectarine tree is embraced by Class 41, Plants, of the U.S. Patent Office Manual of Classification.

BACKGROUND OF THE VARIETY

1. Field of the Invention

Over a substantial number of years I have engaged in an extensive and continuing plant breeding program at my experimental nursery and orchard located near Le Grand, Merced County, Calif.; one purpose of such program being to provide improved varieties of fruit trees. The present variety of nectarine tree resulted from my endeavors in the conduct of such plant breeding program.

2. Prior Varieties

Among the existent varieties of nectarine tree which are known to me, I make particular reference to the Red Diamond (U.S. Plant Pat. No. 3,165), May Grand (U.S. Plant Pat. No. 2,794), and Early Sun Grand (U.S. Plant Pat. No. 1,420) as mentioned hereinafter in this specification.

Origin of the variety: The present variety of nectarine tree was originated by me, in my experimental nursery and orchard located as aforesaid, as an open-pollinated seedling of the Red Diamond; a number of such seedlings having been grown under careful and continuing observation. The present variety was selected by me from such seedlings upon evidencing desirable characteristics for commercial production.

Asexual reproduction of the variety: Subsequent to origination and selection by me of the present variety of nectarine tree, I asexually reproduced it by top-working on orchard trees, and—in maturity—such reproductions ran true to the original tree in all respects.

Summary of the variety: The present variety of nectarine tree is of large-medium size, spreading, hardy, foliated with large, lanceolate, acutely pointed leaves having a crenate margin, medium length petiole, and medium size, alternate, reniform glands, blooms early-medium from hardy, medium length, pointed flower buds, the flowers being large and pink, and the tree is a regular and productive bearer of large, early-ripening, uniform, symmetrical, globose-oblong fruit which is freestone when fully ripe, the fruit having a yellow ground color substantially overspread and highly colored with a dark red, and the flesh is yellow.

The present variety of nectarine is further particularly characterized by early-ripening fruit—as described above—which ripens between the May Grand nectarine and the Early Sun Grand nectarine; the fruit having superior shipping and keeping quality in comparison to like-season fruit of other nectarine and peach varieties.

BRIEF DESCRIPTION OF THE DRAWING

The drawing is an illustration, by photographic reproduction in color, of a twig with leaves, separate fruit, and a separate stone; one fruit being partially cut away to expose the flesh.

DESCRIPTION OF THE VARIETY

The botanical details of this new and distinct variety of nectarine trees—with color definitions (except those in common color terms) referenced to Maerz and Paul Dictionary of Color—are as follows:

Tree:
- *Size.*—Large-medium.
- *Growth.*—Spreading.
- *Hardiness.*—Hardy.
- *Production.*—Productive.
- *Bearing.*—Regular bearer.

Trunk:
- *Size.*—Medium.

Branches:
- *Size.*—Medium.
- *Texture.*—Medium.

Leaves:
- *Size.*—Large. Average length — 6". Average width — 1¼".
- *Form.*—Lanceolate. Acutely pointed.
- *Thickness.*—Medium.
- *Color.*—Top side — medium green (23-J-9). Under side — lighter green (22-K-7).
- *Texture.*—Smooth.
- *Margin.*—Crenate.
- *Petiole.*—Medium length — average ½".
- *Glands.*—Average number — 2–3. Alternate. Medium size. Reniform. Position — on petiole and base of blade.

Flower buds:
*Hardiness.*—Hardy.
*Length.*—Medium.
*Form.*—Pointed.

Flowers:
*Blooming period.*—Early-medium, as compared with other varieties.
*Size.*—Large.
*Color.*—Pink.

Fruit:
*Maturity when described.*—Eating ripe — June 26, 1980.
*Date of first picking.*—June 15, 1980.
*Date of last picking.*—June 25, 1980.
*Size.*—Uniform. Large. Average diameter axially — $2\frac{3}{8}''$. Average transversely in suture. Plane — $2\frac{1}{2}''$.
*Form.*—Uniform. Symmetrical. Globose — oblong.
*Suture.*—Distinct. Extends from base to beyond apex.
*Lips.*—Equal.
*Cavity.*—Rounded. Circular.
*Base.*—Rounded.
*Apex.*—Mammiform.
*Pistil point.*—Apical.

Skin:
*Thickness.*—Medium.
*Texture*—Medium.
*Tendency to crack.*—None noted.
*Color.*—Ground color — yellow (9-L-4) substantially overspread with red (5-K-5) shading to darker red (8-L-6).

Flesh:
*Juice.*—Moderate — abundant.
*Texture.*—Medium. Crisp. Meaty.
*Fibers.*—Few.
*Ripens.*—Evenly.
*Flavor.*—Subacid — mild.
*Aroma.*—Wanting.

*Eating quality.*—Good.
*Color.*—Yellow (9-L-7). Often flecked with red (4-K-5).

Stone:
*Type.*—Freestone when fully ripe.
*Fibers.*—Retains short fiber-like threads along ridges.
*Size.*—Medium — large. Average length — $1\frac{3}{8}''$. Average breadth — $1''$. Average thickness — $\frac{3}{4}''$.
*Form.*—Oblong.
*Base.*—Oblique.
*Sides.*—Equal.
*Ridges.*—Heavily ridged and grooved, with some pitting.
*Pits.*—Circular — elongated.
*Dorsal edge.*—Full.
*Color.*—Tan (12-J-9).
*Tendency to split.*—None noted.

Use: Market; local; dessert; long distance shipping.
Keeping quality: Good.
Resistance to insects and diseases: No unusual susceptibilities noted.
Shipping quality: Good.

The nectarine tree and its fruit herein described may vary in slight detail due to climatic and soil conditions under which the variety may be grown; the present description being of the variety as grown in the Central Valley of California.

I claim:

1. A new and distinct variety of nectarine tree, substantially as illustrated and described, particularly characterized by the regular and productive bearing of large, exteriorly red, yellow fleshed, early ripening, uniform, symmetrical, globose-oblong fruit which is freestone when fully ripe; the fruit ripening between the May Grand nectarine and the Early Sun Grand nectarine, and having superior shipping and keeping quality in comparison to like-season fruit of other nectarine and peach varieties.

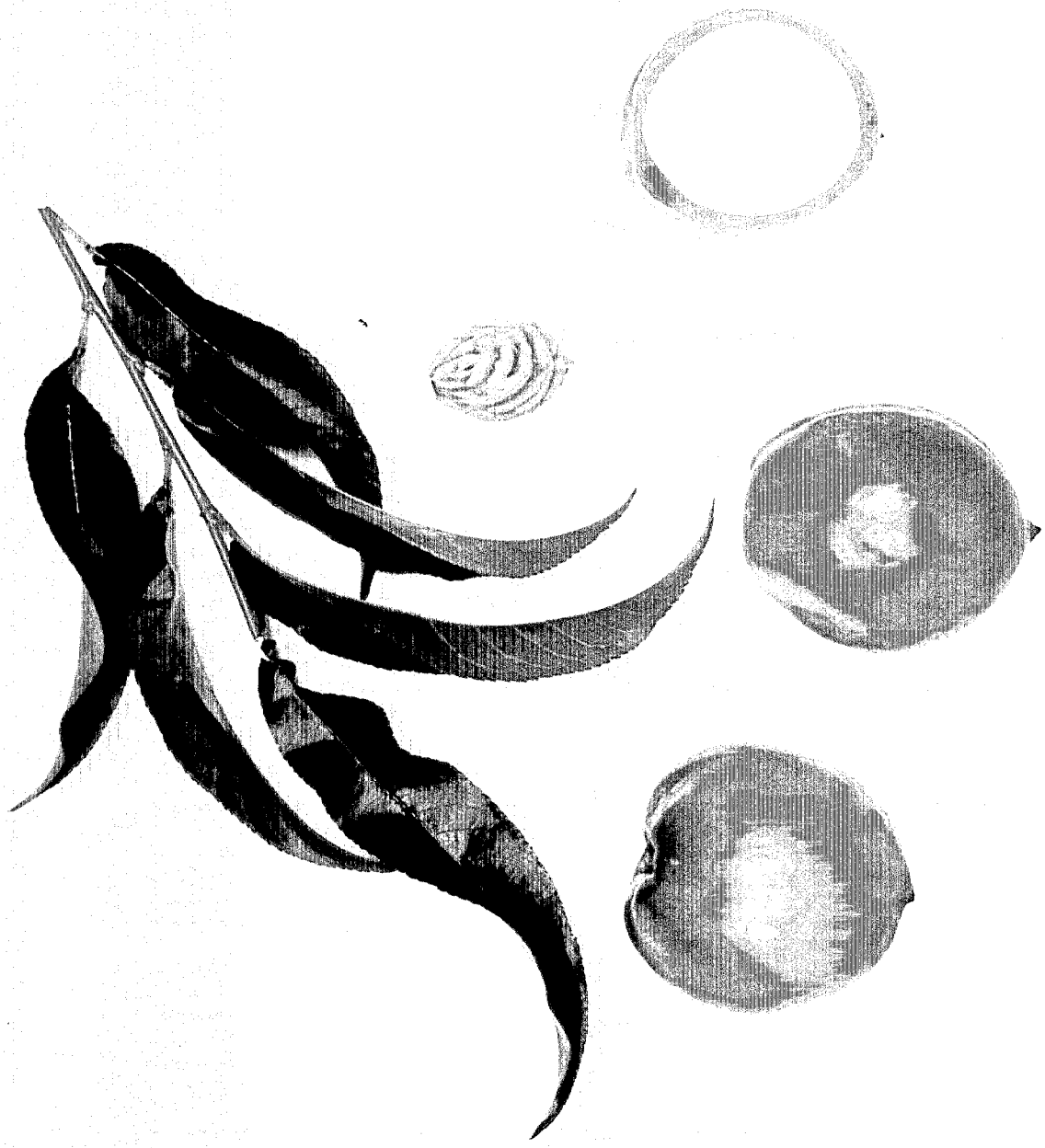

* * * * *